(12) United States Patent
Fichtner et al.

(10) Patent No.: US 9,393,214 B2
(45) Date of Patent: Jul. 19, 2016

(54) CARBON ENCAPSULATED TRANSITION METAL OXIDE NANOCOMPOSITE, A METHOD FOR ITS PREPARATION AND ITS USE IN LI-ION BATTERIES

(71) Applicant: KARLSRUHER INSTITUT FUER TECHNOLOGIE, Karlsruhe (DE)

(72) Inventors: Maximilian Fichtner, Oftersheim (DE); Horst Hahn, Seeheim-Jugenheim (DE); Raju Prakash, Chennai (IN)

(73) Assignee: KARLSRUHER INSTITUT FUER TECHNOLOGIE, Karlsruhe (DE)

(*) Notice: Subject to any disclaimer, the term of this patent is extended or adjusted under 35 U.S.C. 154(b) by 4 days.

(21) Appl. No.: 14/349,074

(22) PCT Filed: Sep. 26, 2012

(86) PCT No.: PCT/EP2012/004042
§ 371 (c)(1),
(2) Date: Apr. 2, 2014

(87) PCT Pub. No.: WO2013/050115
PCT Pub. Date: Apr. 11, 2013

(65) Prior Publication Data
US 2014/0294981 A1  Oct. 2, 2014

(30) Foreign Application Priority Data

Oct. 6, 2011  (EP) .................................... 11008085

(51) Int. Cl.
| | | |
|---|---|---|
| *C01G 49/02* | (2006.01) | |
| *B82Y 30/00* | (2011.01) | |
| *A61K 9/51* | (2006.01) | |
| *C01G 49/08* | (2006.01) | |
| *C09C 1/24* | (2006.01) | |
| *H01M 4/131* | (2010.01) | |
| *H01M 4/36* | (2006.01) | |
| *H01M 4/48* | (2010.01) | |
| *H01M 4/587* | (2010.01) | |
| *A61K 33/26* | (2006.01) | |
| *A61K 47/02* | (2006.01) | |
| *C01B 13/18* | (2006.01) | |
| *H01F 1/01* | (2006.01) | |
| *H01M 4/62* | (2006.01) | |
| *H01M 10/0525* | (2010.01) | |

(52) U.S. Cl.
CPC ............ *A61K 9/5107* (2013.01); *A61K 33/26* (2013.01); *A61K 47/02* (2013.01); *B82Y 30/00* (2013.01); *C01B 13/18* (2013.01); *C01G 49/08* (2013.01); *C09C 1/24* (2013.01); *H01F 1/01* (2013.01); *H01M 4/131* (2013.01); *H01M 4/366* (2013.01); *H01M 4/48* (2013.01); *H01M 4/587* (2013.01); *H01M 4/625* (2013.01); *C01P 2004/64* (2013.01); *C01P 2004/84* (2013.01); *C01P 2004/86* (2013.01); *C01P 2006/10* (2013.01); *C01P 2006/40* (2013.01); *C01P 2006/42* (2013.01); *H01M 4/623* (2013.01); *H01M 10/0525* (2013.01); *Y02E 60/122* (2013.01); *Y10T 428/2991* (2015.01)

(58) Field of Classification Search
CPC ...... C01G 49/08; H01M 4/366; H01M 4/625; B82Y 30/00
See application file for complete search history.

(56) References Cited

U.S. PATENT DOCUMENTS

| | | |
|---|---|---|
| 2010/0035750 A1 | 2/2010 | Yang et al. |
| 2011/0104553 A1 | 5/2011 | Pol et al. |
| 2013/0157055 A1* | 6/2013 | Jenneskens et al. .......... 428/403 |

OTHER PUBLICATIONS

V. Panchal et al.: "Synthesis and characterization of carbon coated nanoparticles produced by a continuous low-pressure plasma process", J Nanopart Res, vol. 13, pp. 3825-3833 (2011).
J. C. Tristao et al.: "Facile preparation of carbon coated magnetic $Fe_3O_4$ particles by a combined reduction/CVD process", Materials Research Bulletin, vol. 46, pp. 748-754 (2011).
H. Liu et al.: "Magnctitc/carbon core-shell nanorods as anodc matcrials for lithium-ion batteries", Electrochemistry Communications, vol. 10, pp. 1879-1882 (2008).
C. F. Wang et al.: "Solid-Phase Synthesis of Carbon-Encapsulated Magnetic Nanoparticles", J. Phys. Chem., vol. 111, pp. 6303-6307 (2007).
B. Banov et al.: "A Study of Nanosize $Fe_3O_4$ Deposited on Carbon Matrix", Journal of Nanoscience and Nanotechnology, vol. 8, pp. 591-594 (2008).
T. Muraliganth et al.: "Facile synthesis of carbon-decorated single-crystalline $Fe_3O_4$ nanowires and their application as high performance anode in lithium ion batteries", Chem. Commun., pp. 7360-7362 (2009).
S. Wang et al.: "$Fe_3O_4$ submicron spheroids as anode materials for lithium-ion batteries with stable and high electrochemical performance", Journal of Power Sources, vol. 195, pp. 5379-5381 (2010).
P. Lian et al.: "Enhanced cycling performance of $Fe_3O_4$-graphene nanocomposite as an anode material for lithium-ion batteries", Electrochimica Acta, vol. 56, pp. 834-840 (2010).
S. Song et al.: "Facile synthesis of $Fe_3O_4$/MWCNTs by spontaneous redox and their catalytic performance", Nanotechnology, vol. 21, pp. 1-6 (2010).

(Continued)

*Primary Examiner* — Gina Justice
(74) *Attorney, Agent, or Firm* — Norman B. Thot (57) ABSTRACT

A nanocomposite includes carbon-encapsulated transition metal oxide nanoparticles. The carbon-encapsulated transition metal oxide nanoparticles comprise a transition metal oxide core having a diameter of from 5 nm to 50 nm covered by a graphitic coating having a thickness of from 1 nm to 5 nm.

9 Claims, 5 Drawing Sheets

(56) References Cited

OTHER PUBLICATIONS

Y. Iie et al.: "Structure and electrochemical performance of nanostructured $Fe_3O_4$/carbon nanotube composites as anodes for lithium ion batteries", Electrochimica Acta, vol. 55, pp. 1140-1144 (2010).

M. Zhang et al.: "Magnetite/graphene composites: microwave irradiation synthesis and enhanced cycling and rate performances for lithium ion batteries", Journal of Materials Chemistry, vol. 20, pp. 5538-5543 (2010).

G. Zhou et al.: "Graphene-Wrapped $Fe_3O_4$ Anode Material with Improved Reversible Capacity and Cyclic Stability for Lithium Ion Batteries", Chemistry of Materials, vol. 22, pp. 5306-5313 (2010).

C. Ban et al.: "Nanostructured $Fe_3O_4$/SWNT Electrode: Binder-Free and High-Rate Li-Ion Anode", Advanced Energy Materials, vol. 22, pp. E145-E149 (2010).

L. Ji et al.: "$Fe_3O_4$ nanoparticle-integrated graphene sheets for high-performance half and full lithium ion cells", Phys. Chem. Chem. Phys., vol. 13, pp. 7170-7177 (2011).

J.-Z. Wang et al.: "Graphene-Encapsulated $Fe_3O_4$ Nanoparticles with 3D Laminated Structure as Superior Anode in Lithium Ion Batteries", Chem. Eur. J., vol. 17, pp. 661-667 (2011).

S. Jin et al.: "Facile synthesis of hierarchically structured $Fe_3O_4$/carbon micro-flowers and their application to lithium-ion battery anodes", Journal of Power Sources, vol. 196, pp. 3887-3893 (2011).

\* cited by examiner

CARBON ENCAPSULATED TRANSITION METAL OXIDE NANOCOMPOSITE, A METHOD FOR ITS PREPARATION AND ITS USE IN LI-ION BATTERIES

CROSS REFERENCE TO PRIOR APPLICATIONS

This application is a U.S. National Phase application under 35 U.S.C. §371 of International Application No. PCT/EP2012/004042, filed on Sep. 26, 2012 and which claims benefit to European Patent Application No. 11008085.0, filed on Oct. 6, 2011. The International Application was published in English on Apr. 11, 2013 as WO 2013/050115 A1 under PCT Article 21(2).

FIELD

The present invention provides a new transition metal oxide nanocomposite, in particular a $Fe_3O_4$ nanocomposite, consisting of carbon encapsulated transition metal oxide nanoparticles and a convenient synthesis to obtain the nanocomposite. The nanocomposite is prepared in a one-step pyrolysis of an oxygen-containing organic transition metal compound without any added solvent or surfactant. The composite can be directly employed as an anode material in a lithium ion cell. The carbon encapsulated $Fe_3O_4$ nanoparticles can moreover be used in biomedical or magnetic applications.

BACKGROUND

Magnetite ($Fe_3O_4$) is an attractive anode material for lithium-ion batteries (LIB) based on the conversion mechanism according to the reaction:

$$Fe_3O_4 + 8Li^+ + 8e^- \leftrightarrow 3Fe + 4Li_2O.$$

$Fe_3O_4$ is characterized by a theoretical capacity of 926 mAhg$^{-1}$, which is far beyond that of the graphite anode (372 mAhg$^{-1}$), eco-friendliness, natural abundance and high electronic conductivity ($2 \times 10^4$ Sm$^{-1}$). Its application in practical lithium-ion batteries (LIB) is, however, hindered due to its low rate performance arising from kinetic limitations, agglomerations and poor cycling stability resulting from significant volume expansion during the redox reaction.

To overcome these problems, Banov et al. (B. Banov, L. Ljutzkanov, I. Dimitrov, A. Trifonova, H. Vasilchina, A. Aleksandrova, A. Mochilov, B. T. Hang, S. Okada and J. I. Yamaki, 2008, J. Nanosci. Nanotech, 591-94) described the synthesis of a $Fe_3O_4$ nanocomposite on a carbon matrix by using a thermal decomposition of iron nitrate. This composite encompasses carbon particles with an average size of about 100-150 nm which are covered by small $Fe_3O_4$ crystallites of a mean size of 16 nm. The modified material yielded a specific capacity of about 400 mAh/g after 30 cycles as an anode in lithium batteries. The synthesis was, however, achieved only by several successive steps including the preparation of the carbon support.

Liu et al. (H. Liu, G. Wang, J. Wang and D. Wexler, 2008, Electrochem. Commun. 1879-82) described a synthesis of carbon coated magnetite ($Fe_3O_4$) core-shell by a multi-step hydrothermal method yielding $Fe_2O_3$ nanorods which were sintered together with citric acid as carbon source. The resulting carbon coated $Fe_3O_4$ nanorods have a diameter in the range of 30-50 nm and a length extending a few 100 nanometers. The prepared $Fe_3O_4$/C core-shell nanorods exhibited an initial lithium storage capacity of 1120 mAh/g and a reversible capacity of 394 mAh/g after 100 cycles.

Muraliganth et al. (T. Muraliganth, A. V. Murugan and A. Manthiram, 2009, Chem. Commun., 7360-62) described a carbon-coating of $Fe_3O_4$-nanowires with glucose-derived carbon-rich polysaccharide in a two-step process by sonication and heating at 400° C. for 3 h. T$Fe_3O_4$-nanowires are, however, complex to synthesize by a time and energy consuming procedure. The use of the $Fe_3O_4$-nanoparticles was not disclosed.

Wang et al. (S. Wang, J. Zhang and C. Chen, 2010, J. Power Sources, 195, 5379-81) described synthesized uniform submicron spheroids of $Fe_3O_4$ by a hydrothermal method. This material has been studied for its capacity as electrode material in Li-ion batteries. While having initially good characteristics, the material lacks stability during long term use, in particular due to the volume changes and agglomeration of the particles.

In another described example, a $Fe_3O_4$-graphene (23 wt.-%) nanocomposite was prepared by a gas/liquid interface reaction (P. Lian, X. Zhu, H. Xiang, Z. Li, W. Yang and H. Wang, 2010, Electrochim. Acta, 834-40). The nanocomposite exhibited good capacity retention (99% after 90 cycles) with a large reversible capacity of 1048 mAh/g. The nanocomposite synthesis is, however, a very complicated, multistep and time consuming process, which required several work-up steps starting from iron nitrate and graphene sheets.

Song et al. (S. Song, R. Rao, H. Yang, H. Liu and A. Zhang, 2010, Nanotechnology, 185602(6pp)) described a fabrication process of $Fe_3O_4$ nanoparticles with a size range of 4-8 nm by a spontaneous redox reaction between $Fe^{3+}$ and multi-walled carbon nanotubes (MWCNTs). In this process, a multi-step pre-conditioning of the MWCNT is required. No electrochemical studies were moreover performed.

He at al. (H. He, L. Huang, J. S. Cai, X. M. Zheng and S. G. Sun, 2010, Electrochim. Acta 55, 1140-44) described the synthesis and electrochemical performance of a nanostructured $Fe_3O_4$/carbon nanotube composite. In this complicated multi-step synthesis process, polyvinyl alcohol (PVA) was used as a hydrogen bond functionalizing agent to modify the multi-walled CNTs. The nanoparticles of $Fe_3O_4$ were then deposited along the sidewalls of the as modified CNTs, the chemical coprecipitation of $(NH_4)_2Fe(SO_4) \cdot 6H_2O$ and $NH_4Fe(SO_4) \cdot 12H_2O$, in the presence of CNTs in an alkaline solution. The final product was obtained by several purification steps, including removal of ammonia, sulphate, unreacted PVA etc.

Zhang et al. (M. Zhang, D. Lei, X. Yin, L. Chen, Q. Li, Y. Wang and T. Wang, 2010, J. Mater. Chem. 20, 5538-43) described the synthesis of magnetite/graphene composites by a microwave irradiation method. In this method, graphene oxide (GO) was first prepared from graphite, then exfoliation was carried out by sonication of the GO. In the next step, the mixture of GO, $Fe(NO_3)_3$, urea and ascorbic acid was refluxed under ambient condition for 1 h with a microwave heater. The method additionally requires several purification and heat treatment steps. The modified electrode material exhibited a reversible capacity of 650 mAh/g after 50 cycles.

Zhou at al. (G. Zhou, D.-W. Wang, F. Li, L. Zhang, N. Li, Z.-S. Wu, L. Wen, G. Q. Lu and H.-M. Cheng, 2010, Chem. Mater. 22, 5306-13) subsequently described the synthesis and electrochemical properties of a graphene-wrapped $Fe_3O_4$ composite. The composite was synthesized by dispersing a graphene nanosheet and $FeCl_3$ in an aqueous solution by sonication, followed by hydrolysis to obtain a FeOOH/graphene sheet. After several purification steps, the resulting product was then reduced to give the desired nanocomposite by heat treatment under inert condition. This material was tested as an anode in lithium batteries and obtained a specific capacitiy of 1026 mAh/g after 30 cycles at a given current density of 35 mA/g.

Ban et al. (C. Ban, Z. Wu, D. T. Gillaspie, L. Chen, Y. Yan, J. L. Blackbrurn and A. C. Dillon, 2010, Adv. Mater. 22, E145-49) recently described high-rate capability binder-free electrode materials consisting of $Fe_3O_4$ and single walled carbon nanotubes (SWCNTs). The best performance was obtained by the nanocomposite containing 95 wt.-% oxide and 5 wt.-% SWCNT. The nanocomposite was prepared by a two-step process, hydrothermal synthesis and vacuum filtration. The most crucial step is the purification/deagglomeration of SWCNTs, which is time consuming. SWCNTs were additionally synthesized by a laser vaporization technique. Both the material and method are very expensive.

Another solution for circumventing the problems of volume changes and agglomeration of $Fe_3O_4$ as an anode material was described by Ji et al. (L. Ji, Z. Tan, T. Kuykendall, S. Aloni, S. Xun, E. Lin, V. Battaglia and Y. Zhang, 2011, Phys. Chem. Chem. Phys. 13, 7170-77) where a nanocomposite of reduced-graphene-oxide (RGO) in which $Fe_3O_4$ nanoparticles are encapsulated was described. The $Fe_3O_4$ nanoparticles are uniformly anchored in the RGO sheets such that severe volume changes or agglomeration of the particles can be avoided. The material was tested as an anode material in Lithium ion batteries. The synthesis of the $Fe_3O_4$-RGO nanocomposite is a time consuming and a multi-step process.

Wang et al. (J.-Z. Wang, C. Zhong, D. Wexler, N. H. Idris, Z.-X. Wang, L.-Q. Chen, H.-K. Liu, 2011, Chem. Eur. J., 17, 661-667) described the preparation of a nanocomposite consisting of $Fe_3O_4$ particles embedded in graphene nanosheets. The nanocomposite was tested as an electrode material in a lithium ion battery where it exposed significantly improved life cycles compared to pure $Fe_3O_4$. The nanocomposite was synthesized in situ starting from graphite and $FeCl_2$ by a multistep hydrothermal method.

The preparation of a further $Fe_3O_4$ nanocomposite in form of hierarchically structured $Fe_3O_4$/carbon micro-flowers was described by Jin et al. (S. Jin, H. Deng, D. Long, X. Liu, L. Zhan, X. Liang, W. Qiao, L. Ling, 2011, J. Power Sources, 196, 3887-3893). This composite consists of nanosized $Fe_3O_4$ crystallites and amorphous carbon which are assembled to micro flowers of 2-5 µm. The paper also discloses a method of a controlled thermal decomposition of an iron-alkoxide precursor for preparing said nanocomposite. This preparation requires energy and time consuming efforts. The $Fe_3O_4$ nanocomposite is proposed and assayed for its capability as an anode material in lithium ion batteries.

A common disadvantage of the state of the art is the lack of an economic one-step solvent-free synthesis which is easy to perform. The cited state of the art does not disclose any nanoparticles or nanocomposites consisting of a transition metal oxide, in particular $Fe_3O_4$, which are encapsulated in a carbon shell.

SUMMARY

An aspect of the present invention is to provide a transition metal oxide-carbon nanocomposite, in particular a $Fe_3O_4$-carbon nanocomposite, which contains transition metal oxide nanoparticles covered with a graphitic carbon onion shell.

Another aspect of the present invention is to provide a simple one-step and solvent-free synthesis of the transition metal oxide-carbon nanocomposite.

A further aspect of the present invention is to provide an anode material for its use in lithium-ion batteries. This anode material should be based on transition metal oxide-carbon nanocomposite, in particular a $Fe_3O_4$-carbon nanocomposite, because of its good capacity, low toxicity and high electronic conductivity. The material should overcome the problems of kinetic limitations, agglomerations and poor cycling stability resulting from significant volume expansion during the redox reaction.

In an embodiment, the present invention provides a nanocomposite which includes carbon-encapsulated transition metal oxide nanoparticles. The carbon-encapsulated transition metal oxide nanoparticles comprise a transition metal oxide core having a diameter of from 5 nm to 50 nm covered by a graphitic coating having a thickness of from 1 nm to 5 nm.

BRIEF DESCRIPTION OF THE DRAWINGS

The present invention is described in greater detail below on the basis of embodiments and of the drawings in which.

DETAILED DESCRIPTION

The present invention provides a nanocomposite containing carbon encapsulated transition metal oxide nanoparticles. These nanoparticles have a core-shell structure, wherein a transition metal core with a diameter from 5 nm to 50 nm is covered by a graphitic carbon coating. The core diameter can, for example, range from 10 nm to 30 nm.

Within the scope of the present invention, a core-shell structure shall mean that the cores, which are formed by substantially spherically-shaped metal oxide nanoparticles, are covered by a coating of several layers of graphitic carbon. This graphitic carbon shell has of a thickness from 1 nm to 5 nm. The interface between the carbon-coating and the metal oxide is characterized by short-range disordered layers.

In an embodiment of the present invention, the nanocomposite can, for example, further comprise carbon nanotubes which are embedded in agglomerates of the carbon encapsulated transition metal oxide nanoparticles.

In an embodiment of the present invention, the nanocomposite can, for example, consist of 70 to 90 wt.-% of transition metal oxide and 10 to 30 wt.-% of carbon in the form of graphitic carbon of the coating and, if present, of carbon nanotubes. The total composition of transition metal oxide and carbon does not exceed 100 wt.-%.

In an embodiment of the present invention, the nanocomposite can, for example, have a porous structure encompassing nanopores of a pore width from 0.1 nm to 2 nm and mesopores having sizes from 2 nm to 50 nm, for example, between 10 nm and 35 nm.

In an embodiment of the present invention, the BET (Brunauer, Emmett, Teller) specific surface area can, for example, range from 80 $m^2g^{-1}$ to 150 $m^2g^{-1}$.

In an embodiment of the nanocomposite of the present invention, the transition metal oxide core can, for example, consist of $Fe_3O_4$ ($Fe_3O_4$—C nanocomposite).

The present invention provides a method to synthesize a carbon encapsulated transition metal oxide nanocomposite as described above. An oxygen-containing organic transition metal compound is submitted to pyrolysis in a hermetically closed vessel under inert gas atmosphere at a temperature from 500 to 800° C. Under these reaction conditions, any presence of organic oxygen is trapped by the metal to form an oxide.

The organic rests of the oxygen-containing organic transition metal compound, which mainly consist of carbon, are substantially reduced to the graphitic coating and to carbon nanotubes. In an embodiment, these organic rests can, for example, be alkoxides, carboxides or carbonyls. In an embodiment, the oxygen-containing organic transition metal compound can, for example, be a transition metal carbonyl. In an embodiment of the present invention, the transition metal carbonyl can, for example, be $Fe(CO)_5$.

In an embodiment of the present invention, the reaction vessel can, for example, be rotated during the reaction. This rotation allows for the gentle mixing of the dry powder during the pyrolysis leading to a homogenous product. The reaction time can, for example, be from 1 to 3 hours.

An advantage of the provided method is that it can be performed in the absence of any solvent. Further additives, such as surfactants, are not required for this synthesis. In an embodiment, the reaction mixture can, for example, contain no or only minute amounts of reducing agents. Under certain conditions, the presence of such agents may lead to the formation of a mixture of transition metal and various transition metal oxides.

By applying the synthesis as described, a crude product is obtained which consists of a nanocomposite containing carbon encapsulated transition metal oxide nanoparticles having a core-shell structure, as defined above, and carbon nanotubes, which have formed in situ during the pyrolytic synthesis.

In an embodiment, the present invention also provides an anode material for lithium-ion batteries containing a nanocomposite as defined herein. The transition metal oxide nanoparticles which are encapsulated within a shell of thin conductible graphitic carbon demonstrate good electrochemical performance. The short-range disordered layers of the interface between the metal oxide core and the carbon shell facilitate the lithium ion transfer from and to the active material in the core.

The network of the core-shell nanoparticles with the nanotubes confers an excellent electronic transport within the electrode. The nanocomposite's morphology is moreover based on the core-shell structure and its porous structure gives the anode material good ionic transport capacities while the composite resists volume changes and agglomeration during the charge and discharge reactions.

It can be advantageous to use the nanocomposite consisting of carbon-encapsulated $Fe_3O_4$ cores ($Fe_3O_4$—C nanocomposite) becasue the iron compounds are abundant and non-toxic while having a good capacity and a high electronic conductivity.

In an embodiment of the present invention, the anode material can, for example, further contain 1-10 wt.-% of carbon black and 1-10 wt.-% of PVDF-HFP (poly(vinylidene fluoride-co-hex afluoropropylene).

When using a $Fe_3O_4$ as transition metal oxide in the carbon-encapsulated nanoparticles, the resulting nanocomposite shows magnetic activity. This magnetic nanocomposite can be used in different applications wherein the magnetic properties combined with the characteristics of the carbon-encapsulated $Fe_3O_4$ nanoparticles are suitable. These characteristics are, for example, no antiferromagnetic coupling between encapsulated $Fe_3O_4$ particles, the non-toxicity, or the chemical passivity of the carbon-shell structure.

The $Fe_3O_4$—C nanocomposite can, for example, be used as a therapeutic agent in medical applications. Upon exposure to a suitable electromagnetic field, the $Fe_3O_4$—C nanocomposite can capture this field and transform it into heat. Upon local application of the nanocomposite into a solid tumor and exposing the area to an appropriate electromagnetic field, the neoplastic tissue can be destroyed non-invasively by heat.

Further magnetic applications of the carbon-encapsulated $Fe_3O_4$ nanoparticles, such as in ferrofluids, are possible.

EXAMPLES

The figures and the following examples are presented to provide a better understanding of the description of procedures and conceptual aspects of the present invention.

Example 1

Synthesis of $Fe_3O_4$—C Nanocomposite $Fe(CO)_5$ was sealed under an argon atmosphere into a stainless steel Swagelok-type reactor. The reactor was placed horizontally inside a rotating quartz-tube setup in a furnace. The tube was rotated (10 rpm) during pyrolysis to obtain a homogeneous mixture. The reactor was heated at a rate of 5° C. $min^{-1}$ to 700° C. and maintained at this temperature for 3 h. The reaction took place under autogenous pressure. After cooling down the reactor to ambient temperature naturally, the remaining pressure was carefully released. A dry fine black powder of $Fe_3O_4$—C nanocomposite produced was collected and used directly without any further treatment.

Example 2

Analysis of $Fe_3O_4$—C Nanocomposite

Figure 1:
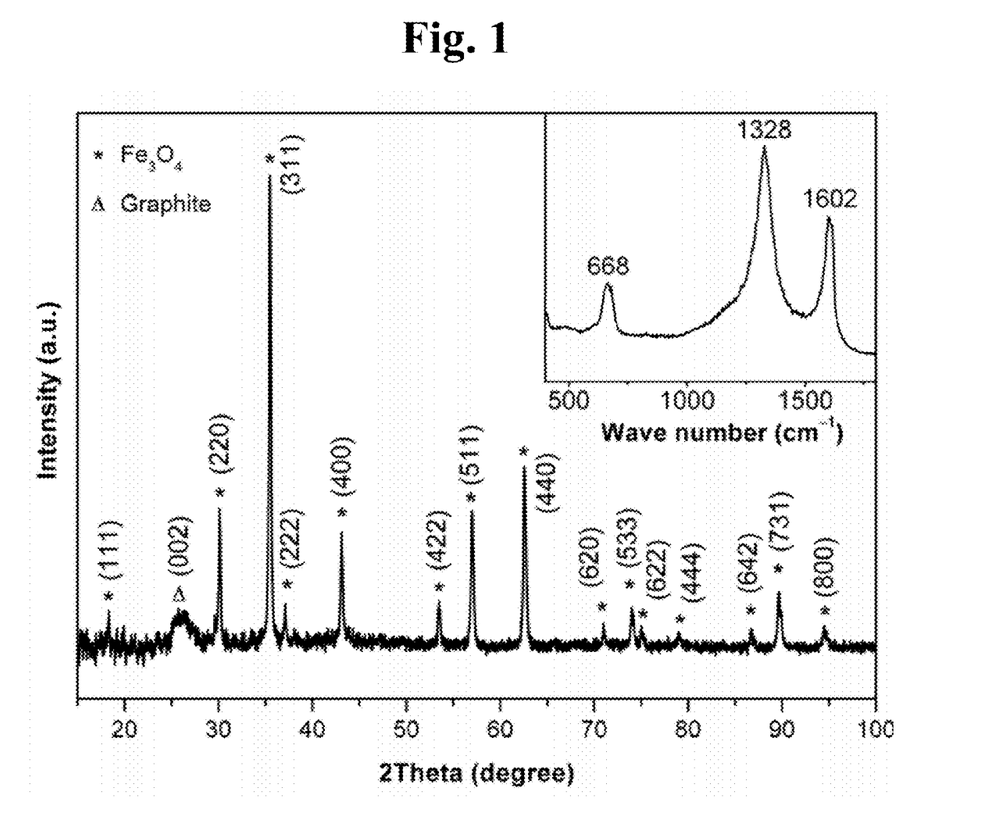
FIG. 1 shows an X-ray powder diffraction (XRD) pattern and a Raman spectrum (inset) of a $Fe_3O_4$—C nanocomposite.

The X-ray powder diffraction (XRD) pattern and the Raman spectrum of the nanocomposite prepared are shown in FIG. 1. All the diffraction peaks can be indexed to two well-defined phases, a hexagonal phase graphitic carbon [26.4° (002)] and a cubic phase $Fe_3O_4$. No detectable signals for metallic iron or other oxides were observed in the XRD pattern, indicating that the oxidation reaction was complete and formed only the selective oxide. The Scherrer analysis was performed on 220, 311, 400, 511 and 440 Bragg peaks of $Fe_3O_4$, and the mean crystallite size was calculated as 14 nm.

The Raman spectrum of the nanocomposite exhibits two bands at 1328 and 1602 $cm^{-1}$, which are characteristic of the D (disorder-induced phonon mode 15) and G (graphitic lattice mode $E_{2g}^{16}$) bands of carbon, respectively. The intensity ratio $I_G/I_D$ of 0.7 indicated that a significant quantity of disordered carbon is also present in the nanocomposite. The $A_{1g}$ vibration mode of $Fe_3O_4$ peak additionally appeared at 668 $cm^{-1}$, which agrees well with the literature value for pure as well as graphene encapsulated $Fe_3O_4$. The infra-red spectrum of the nanocomposite exhibits a broad band at 560 $cm^{-1}$ which is typical for the Fe—O vibration of $Fe_3O_4$.

Figure 2:
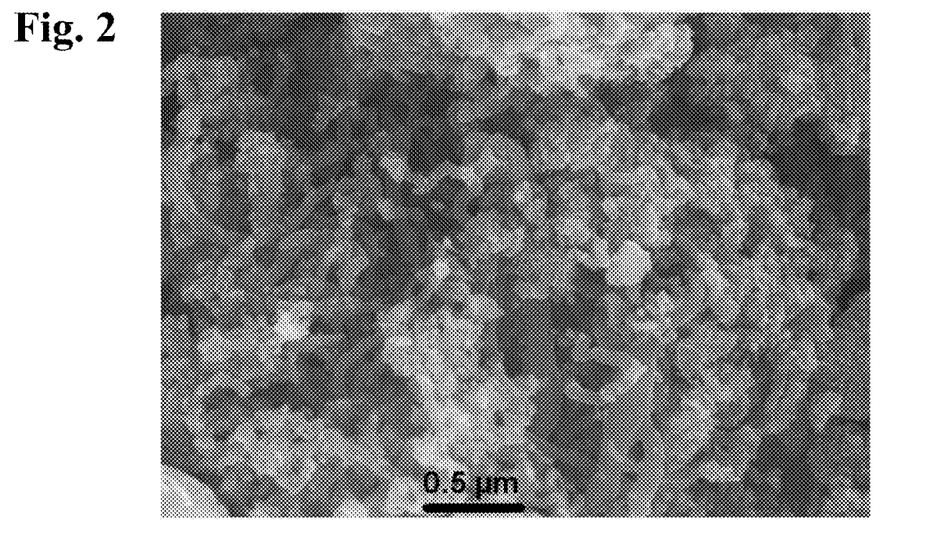
FIG. 2 shows a scanning electron microscope (SEM) image of a $Fe_3O_4$—C nanocomposite.

The scanning electron microscope (SEM) image of $Fe_3O_4$—C nanocomposite (FIG. 2) shows that the material consists of nanotubes and nanogranular structures interlinking with each other. The diameters of the tubes are in the range between 10 to 100 nm and their lengths varied up to several micrometers. A large number of tubes were encapsulated with iron oxide nanoparticles at their tips. However, in some longer tubes, the particles were embedded in several places within the tube.

Figure 3:
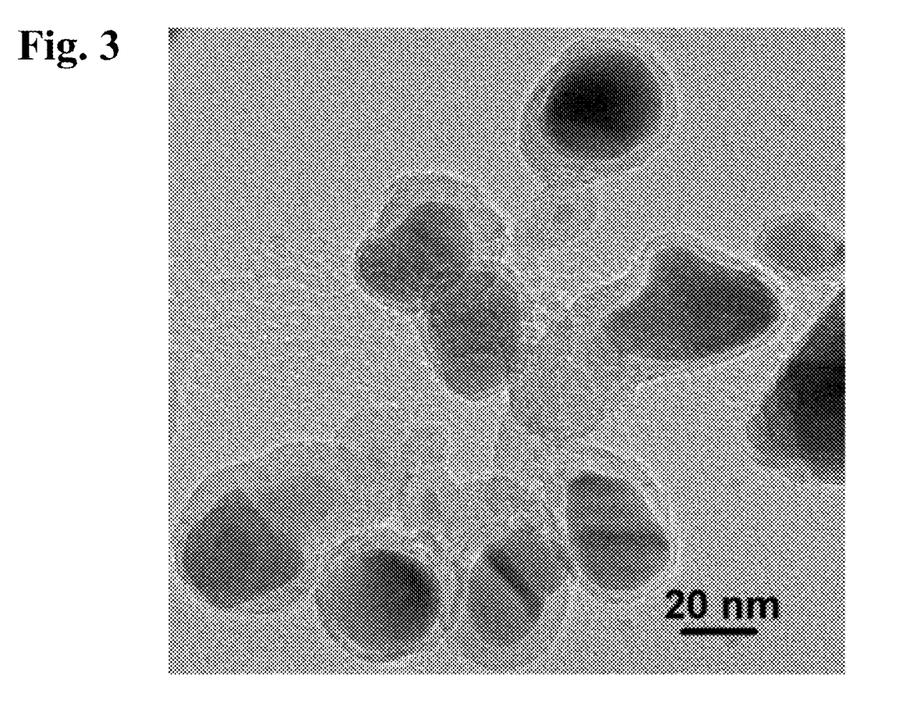
FIG. 3 shows a high resolution transmission electron microscopy (HRTEM) image of a $Fe_3O_4$—C nanocomposite.
Figure 4:
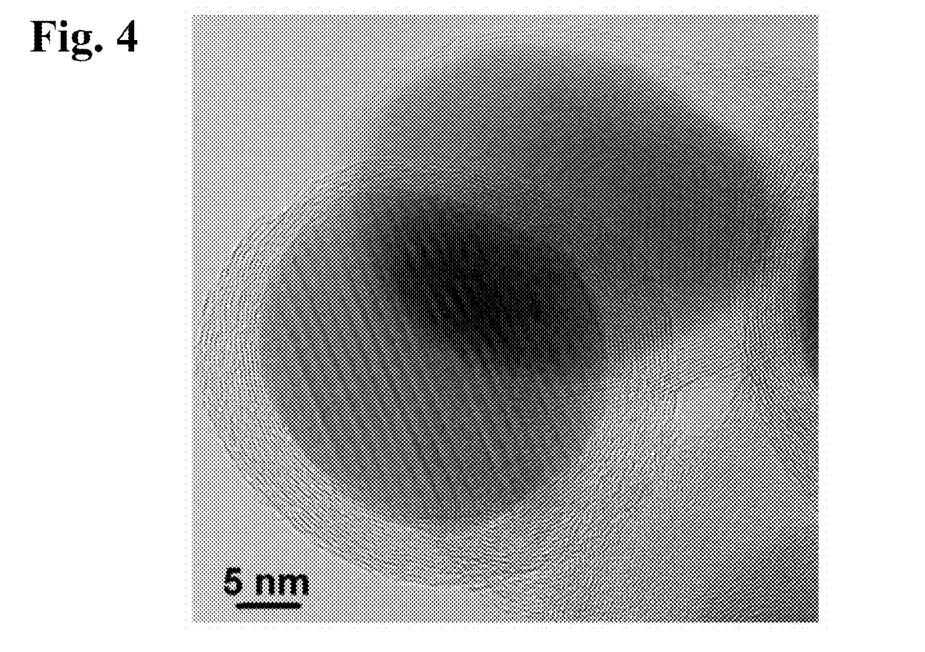
FIG. 4 shows a high resolution transmission electron microscopy (HRTEM) image of a $Fe_3O_4$—C nanocomposite.
Figure 5:
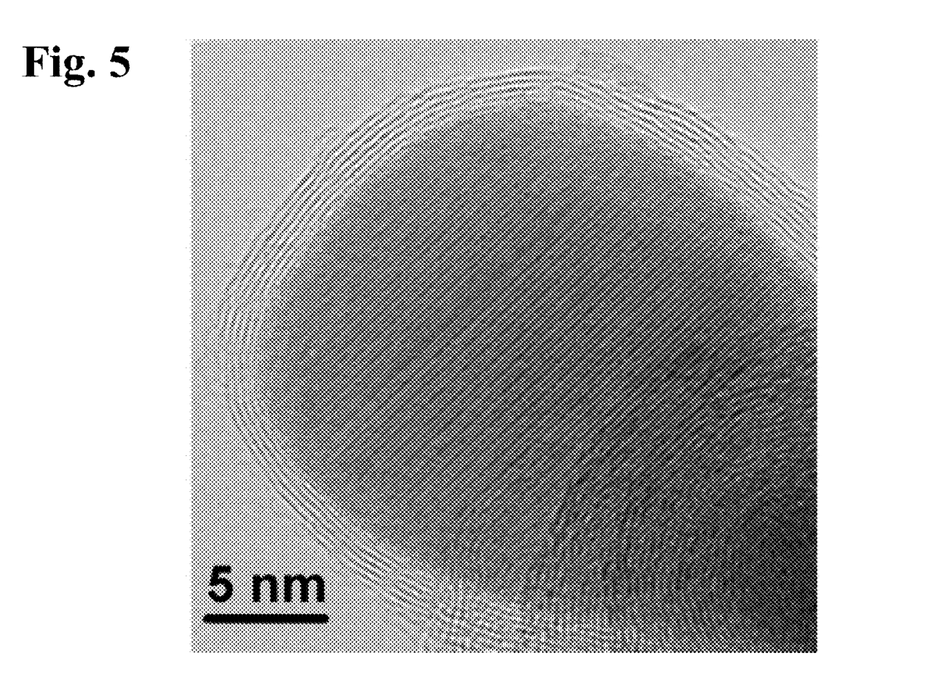
FIG. 5 shows a high resolution transmission electron microscopy (HRTEM) image of a $Fe_3O_4$—C nanocomposite.

High resolution transmission electron microscopy (HR-TEM) images (FIGS. 3 to 5) of the nanogranular region of the composite confirmed the presence of core-shell structure containing $Fe_3O_4$ cores and graphitic onions shells. The interface between graphitic carbon and $Fe_3O_4$ with short-range disordered layers can be observed. The $Fe_3O_4$ particles are coated with three to six layers of graphitic carbon with an average coating thickness of about 3 nm. A few $Fe_3O_4$ particles are, however, surrounded by several layers of carbon.

Figure 6:
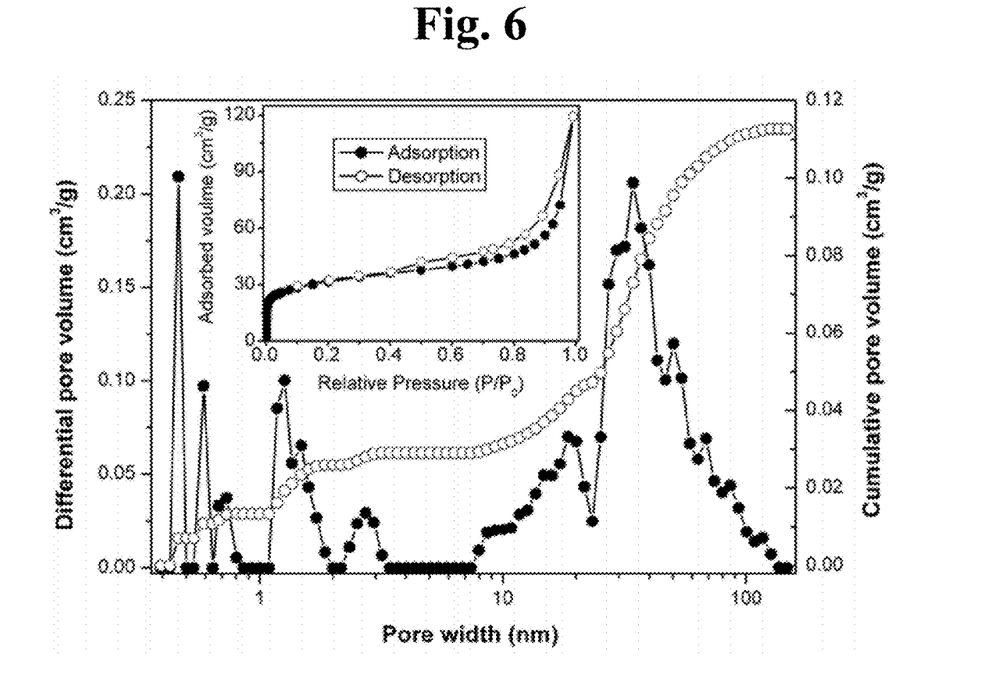
FIG. 6 shows a cumulative and a differential pore width profile of a $Fe_3O_4$—C nanocomposite.

FIG. 6 shows the differential pore volume (filled circles) and the cumulative pore volume (open circles). The nitrogen adsorption-desorption measurement indicates a mesoporous nature of the material. A sharp increase of the adsorbed gas at very low relative-pressures additionally suggests the presence of nanopores (pore width<2 nm). The nano- and mesoporous volumes were determined to be 0.012 and 0.05 $cm^3g^{-1}$, respectively. The differential pore volume (filled circles in FIG. 6) estimated from the adsorption branch of isotherm using Density Functional Theory model suggests that the mesopore sizes were distributed between 10 and 35 nm. The BET (Brunauer, Emmett, Teller) specific surface area was calculated to be as high as 110.6 $m^2g^{-1}$ (open circles in FIG. 6).

It has been well established that porous electrode materials facilitated lithium ion diffusion to active sites with less resistance and also withstand the volume change during charge/discharge cycling. The nano- and mesopores of the $Fe_3O_4$—C nanocomposite could thus act as buffer against the volume change during redox cycle, which would lead to an enhanced cyclic performance as an anode material for lithium ion batteries.

Example 3

Electrochemical Properties

Figure 7:
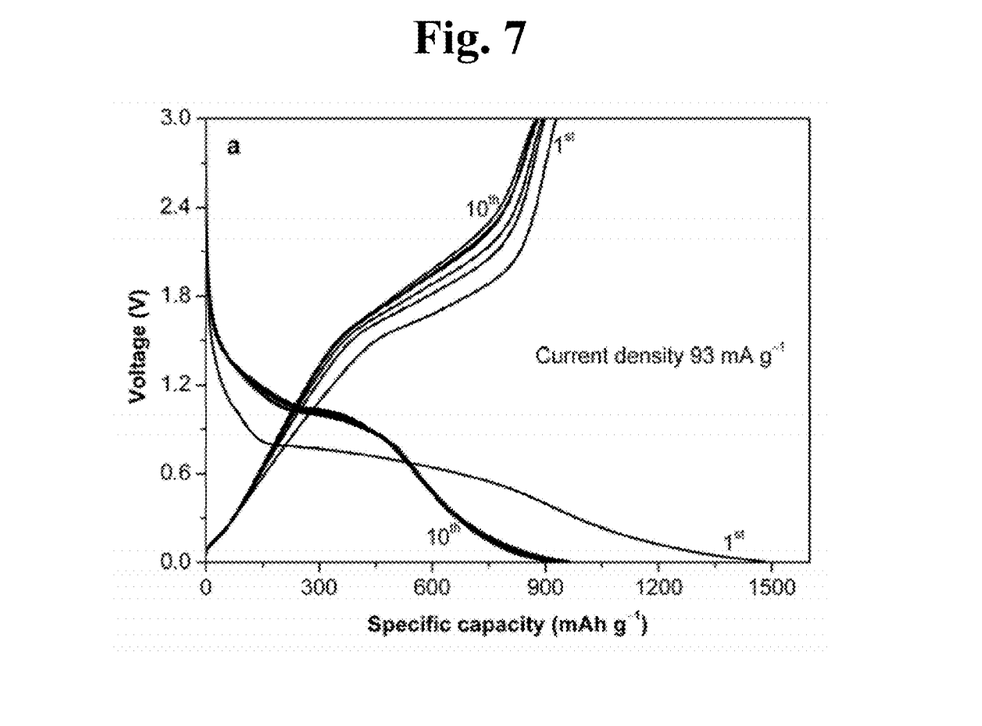
FIG. 7 shows charge/discharge curves of an $Fe_3O_4$—C nanocomposite electrode.

The electrochemical performance of the $Fe_3O_4$—C nanocomposite anode has been evaluated with respect to lithium metal. FIG. 7 shows a typical galvanostatic profile for a $Fe_3O_4$—C nanocomposite cell cycled between 3 and 0.005 V at 93 $mAg^{-1}$. The obtained charge/discharge profiles are analogous to that of various $Fe_3O_4$ electrodes tested at similar current and voltage ranges. During the first discharge, the potential dropped abruptly down to about 0.8 V, which can be ascribed to the reaction of $Fe_3O_4 + xLi \rightarrow Li_xFe_3O_4$. The long plateau corresponds to the conversion reaction and the sloping part of the discharge curve can be assigned for the formation of solid electrolyte interface (SEI) layer, as well as gel-like film formed by the reaction of $Fe^0$ and electrolyte. The electrode exhibits a first discharge capacity of 1480 $mAhg^{-1}$ based on the total composite weight and the first charge capacity of 960 $mAhg^{-1}$. The capacity decreases marginally over the first few cycles and then stabilizes at about 920 $mAhg^{-1}$ in the subsequent 50 cycles. The coulombic efficiency after the first cycle remained nearly 100% until 50 cycles.

Figure 8:
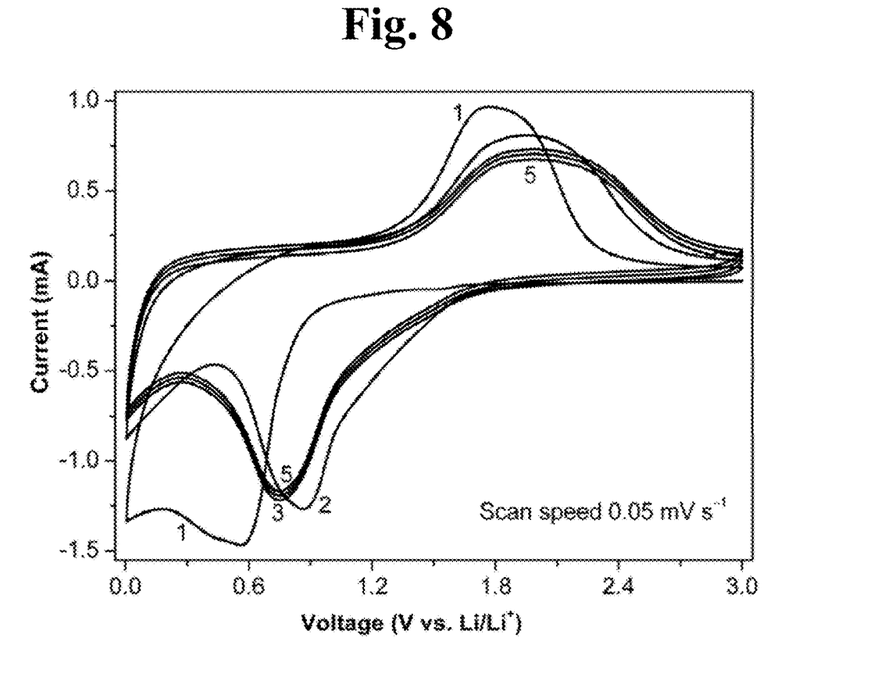
FIG. 8 shows a cyclic voltammogram of an $Fe_3O_4$—C nanocomposite electrode.

The cyclic voltammogram of $Fe_3O_4$—C nanocomposite is parallel to that of other $Fe_3O_4$ electrodes, showing a cathodic wave at 0.56 V and an anodic wave at 1.78 V corresponding to a $Fe^{3+}/Fe^{2+}$ to $Fe^0$ redox couple. The irreversible wave at 0.4 V can be ascribed to the SEI formation. In the subsequent cycles, the reversible waves shifted slightly to positive potentials. The CV curves after third successive scans nearly overlapped, which reveal the good reversibility of the composite electrode.

Figure 9:
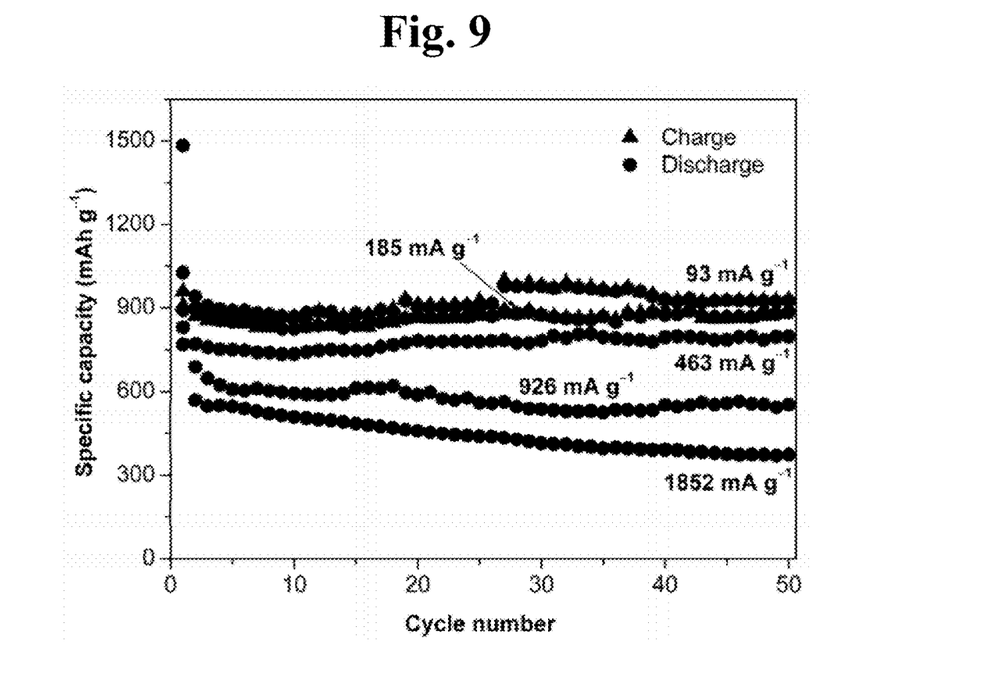
FIG. 9 shows a rate performance profile of an $Fe_3O_4$—C nanocomposite electrode.

Besides the cyclic stability, it also exhibits a moderate rate capability performance (FIG. 9). Current densities below 926 $mAg^1$, the electrode exhibited good cyclic performances and excellent capacity retention. When the electrode cycled at 1852 and 2780 $mAg^1$, the observed capacity retentions between the $3^{rd}$ and $50^{th}$ cycles were about 72 and 63%, respectively.

A comparative SEM image of the electrode cycled for 50 cycles at 93 $mAg^{-1}$ has shown similar morphology as the original composite, indicating that the structure remains integrated during cycling. The good electrochemical performance of the composite can be attributed to its morphology and porous structure. The networking of nanotubes and core-shell structure containing active materials combined with nano and mesopores may in particular help providing better electronic and ionic transport, as well as withstanding the volume change during the reaction.

The present invention is not limited to embodiments described herein; reference should be had to the appended claims.

What is claimed is:

1. A nanocomposite comprising carbon nanotubes embedded in the nanocomposite and carbon-encapsulated transition metal oxide nanoparticles comprising a transition metal oxide core having a diameter of from 5 nm to 50 nm covered by a graphitic coating having a thickness of from 1 nm to 5 nm.

2. The nanocomposite as recited in claim 1, wherein the nanocomposite consists of 70 to 90 wt.-% of a transition metal oxide and 10 to 30 wt.-% of carbon.

3. The nanocomposite as recited in claim 2, wherein the transition metal oxide is $Fe_3O_4$.

4. The nanocomposite as recited in claim 1, wherein the nanocomposite comprises nanopores having a pore size of from 0.1 nm to 2 nm, and mesopores having a pore size of from 2 nm to 50 nm.

5. A method of synthesizing the nanocomposite as recited in claim 1, the method comprising:
    providing an oxygen-containing organic transition metal compound in a closed vessel under an inert gas atmosphere; and
    pyrolysing the oxygen-containing organic transition metal compound at a temperature of from 500° C. to 800° C.

6. The method as recited in claim 5, further comprising rotating the closed vessel during the pyrolysing.

7. The method as recited in claim 5, wherein the pyrolysing is performed for a time of from 1 to 3 hours.

8. The method as recited in claim 5, wherein the oxygen-containing organic transition metal compound is a transition metal carbonyl.

9. The method as recited in claim 8, wherein the transition metal carbonyl is $Fe(CO)_5$.

* * * * *